(12) United States Patent
Tsubouchi et al.

(10) Patent No.: US 7,507,867 B2
(45) Date of Patent: Mar. 24, 2009

(54) BICYCLO[2.2.1] HEPTANE DERIVATIVE

(75) Inventors: Toshiyuki Tsubouchi, Chiba (JP); Yukio Yoshida, Chiba (JP); Motohisa Ido, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 536 days.

(21) Appl. No.: 10/481,647

(22) PCT Filed: Jun. 12, 2002

(86) PCT No.: PCT/JP02/05863

§ 371 (c)(1), (2), (4) Date: Dec. 22, 2003

(87) PCT Pub. No.: WO03/000632

PCT Pub. Date: Jan. 3, 2003

(65) Prior Publication Data

US 2004/0171898 A1 Sep. 2, 2004

(30) Foreign Application Priority Data

Jun. 22, 2001 (JP) .............................. 2001-189422

(51) Int. Cl.
  *C07C 13/40* (2006.01)
  *C09J 11/06* (2006.01)
  *C10M 105/04* (2006.01)

(52) U.S. Cl. ................................. 585/20; 585/1; 585/16

(58) Field of Classification Search ....................... 585/20
  See application file for complete search history.

(56) References Cited

U.S. PATENT DOCUMENTS 5,126,065 A * 6/1992 Tsubouchi et al. .......... 508/591
6,319,879 B1 * 11/2001 Yoshida et al. .............. 508/110
6,841,713 B2 * 1/2005 Tsubouchi et al. .......... 585/664
7,015,178 B2 * 3/2006 Koga et al. ................. 508/463

FOREIGN PATENT DOCUMENTS

EP 161112 11/1985
EP 968987 1/2000

OTHER PUBLICATIONS

Edited by The Adhesion Society of Japan, "Secchaku Handbook Dai 2 Han", The Nikkan Kogyo Shinbun, Ltd., 1980, pp. 423 to 424.

* cited by examiner

*Primary Examiner*—Ellen M. McAvoy
(74) *Attorney, Agent, or Firm*—Oblon, Spivak, McClelland, Maier & Neustadt, P.C.

(57) ABSTRACT

A bicyclo[2.2.1]heptane derivative represented by following general formula (1):

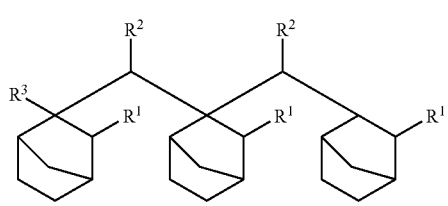

wherein $R^1$ and $R^2$ each represent hydrogen atom or methyl group, and $R^3$ represents methyl group or ethyl group. The derivative is suitable as a high viscosity hydrocarbon base material used for tackfiers for adhesives and process oils for rubber and resins.

16 Claims, 4 Drawing Sheets

BICYCLO[2.2.1] HEPTANE DERIVATIVE

TECHNICAL FIELD

The present invention relates to a bicyclo[2.2.1]heptane derivative and, more particularly, to a bicyclo[2.2.1]heptane derivative suitable as a high viscosity hydrocarbon base material used for tackfiers for adhesives and process oils for rubber and resins.

BACKGROUND ART

High viscosity hydrocarbon base materials are used for tackfiers for adhesives and process oils for rubber and resins. As the high viscosity hydrocarbon base material, polybutene, ethylene-propylene oligomers and poly-α-olefins have heretofore been used. However, the above base materials have a drawback in that materials which can be used in combination are restricted due to poor compatibility with various organic substances.

When workability in mixing is considered, it is preferable that viscosity is small during mixing so that the mixing is facilitated. Therefore, it is preferable that the base material has a viscosity-temperature characteristic such that viscosity is low at high temperatures (during the mixing) and high at temperatures around the room temperature (during the use). In other words, a small viscosity index is preferable. The conventional base materials described above have a drawback in that the viscosity index is 100 or greater and the change in viscosity with temperature is small.

The present invention has been made to overcome the above drawbacks and has an object of providing a compound exhibiting excellent compatibility with various organic substances and has a small viscosity index.

DISCLOSURE OF THE INVENTION

As the result of intensive studies by the present inventors, it was found that specific bicyclo[2.2.1]heptane derivatives exhibit the desirable properties described above as the object of the present invention. The present invention has been completed based on this knowledge.

The present invention provides:
1. A bicyclo[2.2.1]heptane derivative represented by following general formula (1):

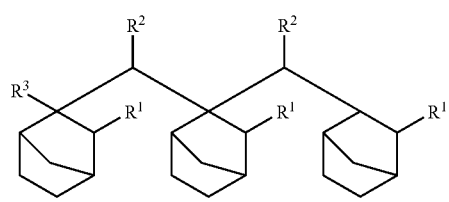

wherein $R^1$ and $R^2$ each represent hydrogen atom or methyl group, and $R^3$ represents methyl group or ethyl group; and
2. A bicyclo[2.2.1]heptane derivative according to Claim 1, which is 3-methyl-2-[(3-methylbicyclo[2.2.1]hept-2-yl)methyl]-2-[(2,3-dimethylbicyclo[2.2.1]-hept-2-yl)methyl]bicyclo[2.2.1]heptane.

THE MOST PREFERRED EMBODIMENT TO CARRY OUT THE INVENTION

Figure 1:
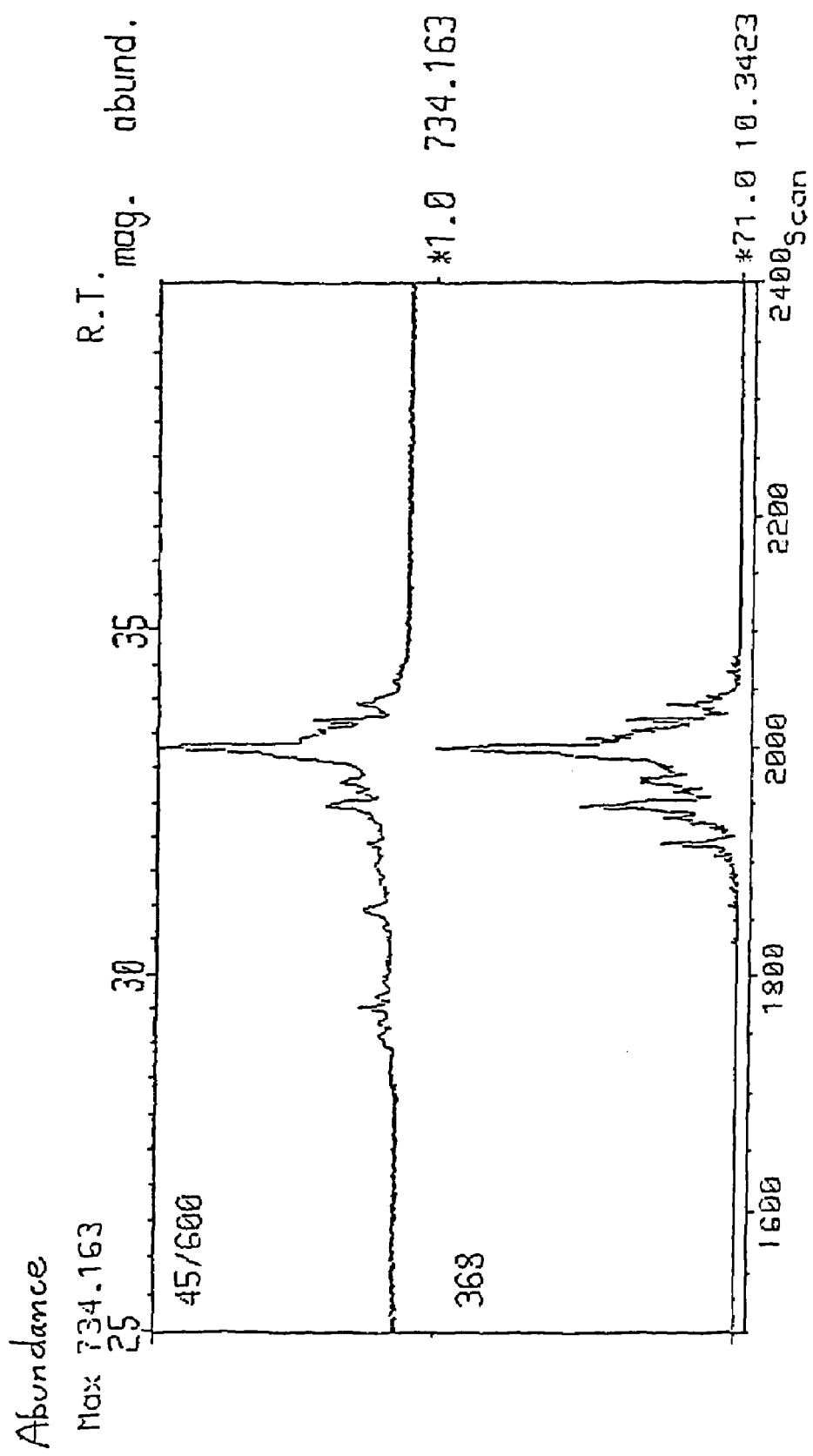
FIG. 1 shows a mass chromatogram of a hydrogenation product of a trimer.

The embodiments of the present invention will be described in the following.

The bicyclo[2.2.1]heptane derivative of the present invention is represented by the above general formula (1). Examples of the derivative include 3-methyl-2-[(3-methylbicyclo[2.2.1]hept-2-yl)methyl]-2-[(2,3-dimethylbicyclo[2.2.1]hept-2-yl)methyl]bicyclo[2.2.1]heptane, 2-[(bicyclo[2.2.1]hept-2-yl)methyl]-2-[(2-methylbicyclo[2.2.1]hept-2-yl)methyl]bicyclo-[2.2.1]heptane and 2-[(bicyclo[2.2.1]hept-2-yl)ethyl]-2-[(2-ethylbicyclo-[2.2.1]hept-2-yl)ethyl]bicyclo[2.2.1]heptane. From the standpoint of the effect exhibited by the compound, 3-methyl-2-[(3-methylbicyclo[2.2.1]-hept-2-yl)methyl]-2-[(2,3-dimethylbicyclo[2.2.1]hept-2-yl)methyl]bicyclo-[2.2.1]heptane is preferable. The chemical structure of this compound is expressed by the following formula (2).

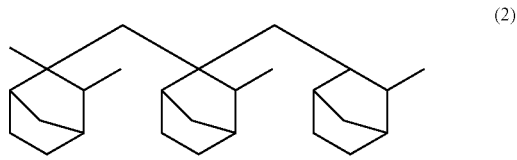

As the preferable process for producing the bicyclo[2.2.1]heptane derivative of the present invention, a material olefin can be trimerized, hydrogenated and distilled, successively.

Examples of the material olefin include bicyclo[2.2.1]heptanes having methyl group and methylene group, bicyclo[2.2.1]heptanes having methylene group, bicyclo[2.2.1]heptanes having ethylidene group, bicyclo[2.2.1]hept-2-enes having methyl group and bicyclo[2.2.1]-hept-2-enes having ethyl group. From the standpoint of the effect exhibited by the formed compound, 2,3-dimethylbicyclo[2.2.1]hept-2-ene and 3-methyl-2-methylenebicyclo[2.2.1]heptane are preferable.

The above trimerization includes trimerization of an olefin of a single type and cotrimerization of a plurality of olefins of different types.

The above trimerization is conducted, in general, in the presence of a catalyst and, where necessary, with the addition of a solvent.

As the catalyst used for the trimerization, in general, an acidic catalyst is used. Examples of the catalyst include solid acids such as zeolite, active clay, montmorillonite and ion exchange resins; mineral acids such as hydrofluoric acid and polyphosphoric acid; organic acids such as triflic acid; Lewis acids such as aluminum chloride, titanium tetrachloride, iron trichloride, tin tetrachloride, boron trifluoride, complexes of boron trifluoride, boron tribromide, aluminum bromide, gallium chloride and gallium bromide; and organoaluminum compounds such as triethylaluminum, diethylaluminum chloride and ethylaluminum dichloride. Since it is preferable that the trimerization is conducted at low temperatures, polyphosphoric acid, boron trifluoride, complexes of boron trifluoride, tin tetrachloride, titanium tetrachloride and aluminum chloride are preferable.

The amount of the catalyst is not particularly limited. In general, the amount of the catalyst is selected in the range of 0.1 to 100% by mass based on the amount of the material olefin.

For the trimerization, a solvent is not always necessary. A solvent may be used from the standpoint of handling of the material olefin and the catalyst in the reaction and the adjustment of the procedures of the process. Examples of the solvent include saturated hydrocarbons such as various types of pentane, various types of hexane, various types of octane, various types of nonane and various types of decane; alicyclic hydrocarbons such as cyclopentane, cyclohexane, methylcyclohexane and decaline; ether compounds such as diethyl ether and tetrahydrofuran; compounds having halogens such as methylene chloride and dichloroethane; and nitro compounds such as nitromethane and nitrobenzene.

The trimerization is conducted in the presence of the catalyst described above. The temperature of the trimerization is, in general, 200° C. or lower and preferably 100° C. or lower so that the isomerization is suppressed. When the economy is also considered, it is preferable that the temperature is −70° C. or higher and more preferably −30° C. or higher.

The conditions of the reaction can be suitably set in accordance with the types of the catalyst, additives and the like. The pressure of the reaction is, in general, the atmospheric pressure, and the time is, in general, in the range of 0.5 to 10 hours.

The trimer of the material olefin obtained as described above is hydrogenated, and the hydrogenation product of the trimer, i.e., the object compound, is obtained.

The hydrogenation is, in general, conducted in the presence of a catalyst. Examples of the catalyst include hydrogenation catalysts such as nickel, ruthenium, palladium, platinum, rhodium and iridium supported on supports such as diatomaceous earth, silica-alumina and active carbon; and Raney nickel. Among these catalysts, supported nickel catalysts such as nickel/diatomaceous earth and nickel/silica-alumina are preferable. The amount of the catalyst is, in general, in the range of 0.1 to 100% by mass based on the amount of the trimerization product described above.

The hydrogenation can be conducted in the absence or in the presence of solvents similarly to the trimerization. Examples of the solvent include saturated hydrocarbons such as various types of pentane, various types of hexane, various types of octane, various types of nonane and various types of decane; and alicyclic hydrocarbons such as cyclopentane, cyclohexane, methylcyclohexane and decaline.

The temperature of the hydrogenation is, in general, in the range of 100 to 300° C. and preferably in the range of 160 to 280° C. When the temperature is lower than 100° C., the hydrogenation does not proceed sufficiently, occasionally. When the temperature exceeds 300° C., the yield decreases due to decomposition. The pressure of the reaction is, in general, in the range of the atmospheric pressure to 20 MPa·G and preferably in the range of the atmospheric pressure to 10 MPa·G. The time of the reaction is, in general, in the range of 1 to 10 hours.

The formed hydrogenation product can be purified by distillation.

The present invention will be described more specifically with reference to examples in the following. However, the present invention is not limited to the examples.

EXAMPLE 1

Into a 2 liter autoclave made of stainless steel, 561 g (8 moles) of crotonaldehyde and 352 g (2.67 moles) of dicyclopentadiene were placed, and the reaction was allowed to proceed under stirring at 170° C. for 3 hours. After the obtained reaction solution was cooled to the room temperature, 18 g of a Raney nickel catalyst (manufactured by KAWAKEN FINE CHEMICALS Co., Ltd.; M-300T) was added, and the hydrogenation was conducted under a hydrogen pressure of 0.88 MPa·G at a temperature of 150° C. for 4 hours. After the reaction mixture was cooled and the catalyst residue was removed by filtration, the filtrate was distilled under a reduced pressure, and 565 g of a fraction of 105° C./2.67 kPa was obtained. As the result of the analysis of the obtained fraction based on the mass spectrum and the nuclear magnetic resonance spectra, the fraction was identified to be 2-hydroxymethyl-3-methylbicyclo[2.2.1]-heptane.

Into a flow type atmospheric reaction tube made of quartz and having a diameter of 20 mm and a length of 500 mm, 20 g of γ-alumina (manufactured by NIKKI CHEMICAL Co., Ltd.; N612) was placed. The dehydration was conducted at a temperature of 285° C. and a weight hourly space velocity (WHSV) of 1.1 hr$^{-1}$, and 490 g of a dehydration product of 2-hydroxymethyl-3-methylcyclo[2.2.1]heptane was obtained. The product contained 2-methylene-3-methylbicyclo[2.2.1]heptane and 2,3-dimethylbicyclo[2.2.1]hept-2-ene.

Preparation of a Hydrogenation Product of a Trimer

Figure 2:
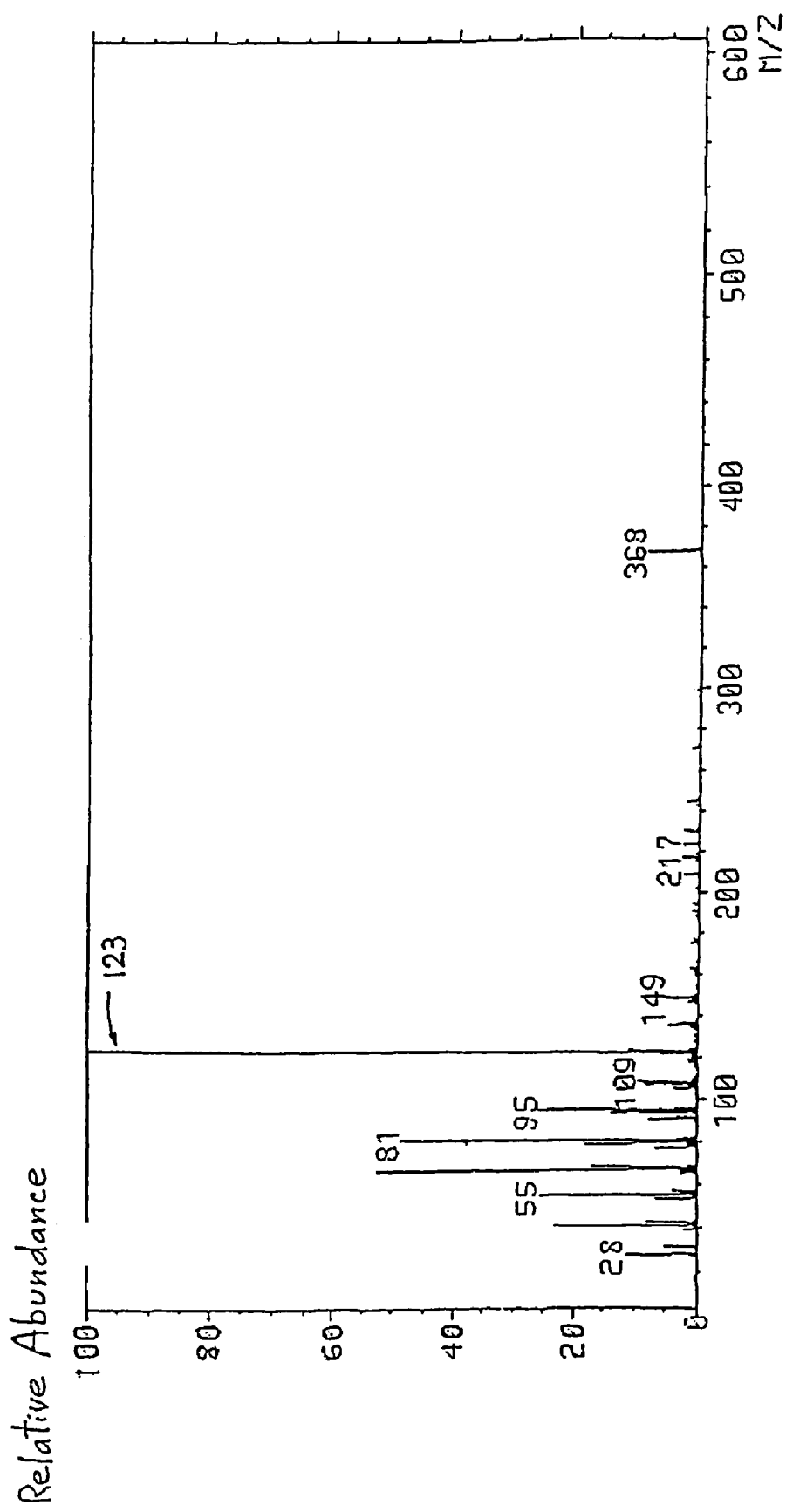
FIG. 2 shows a mass spectrogram of a hydrogenation product of a trimer.
Figure 3:
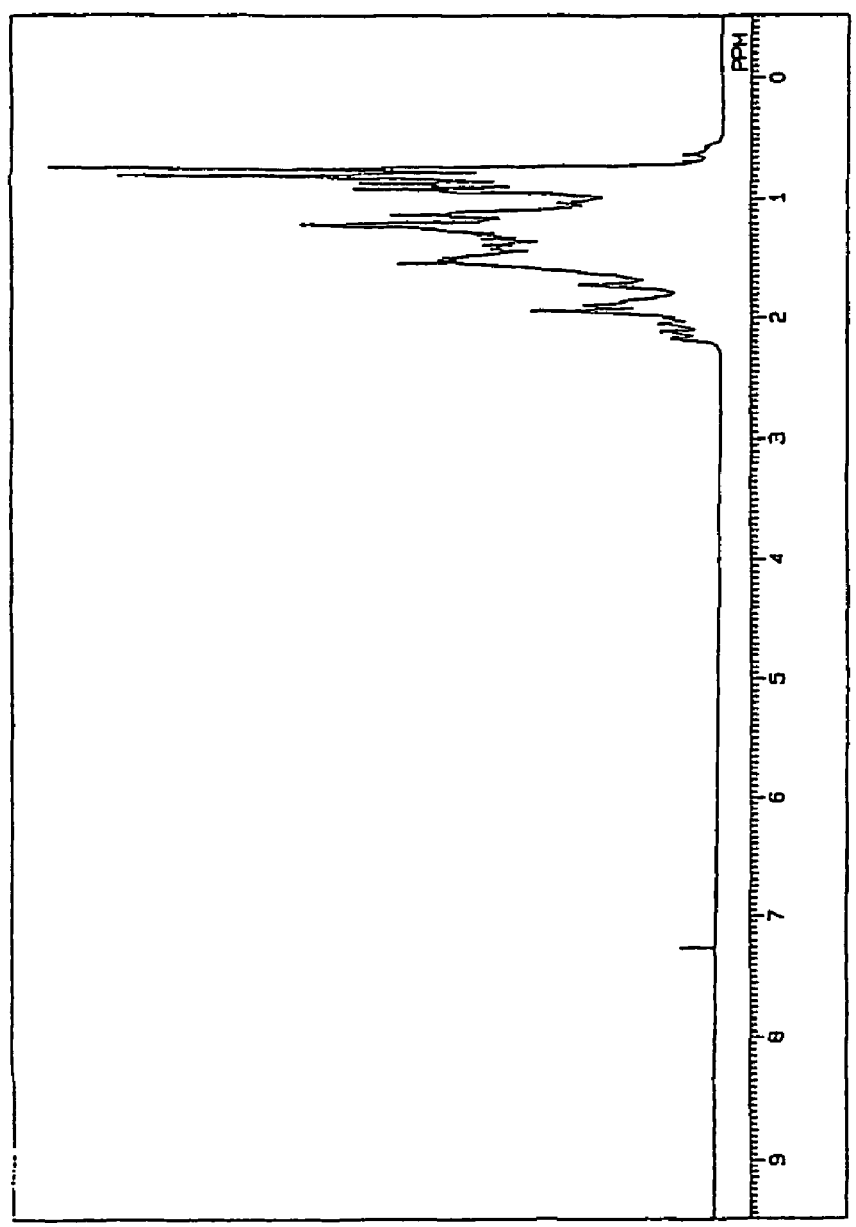
FIG. 3 shows a $^1$H-NMR spectrogram of a hydrogenation product of a trimer.
Figure 4:
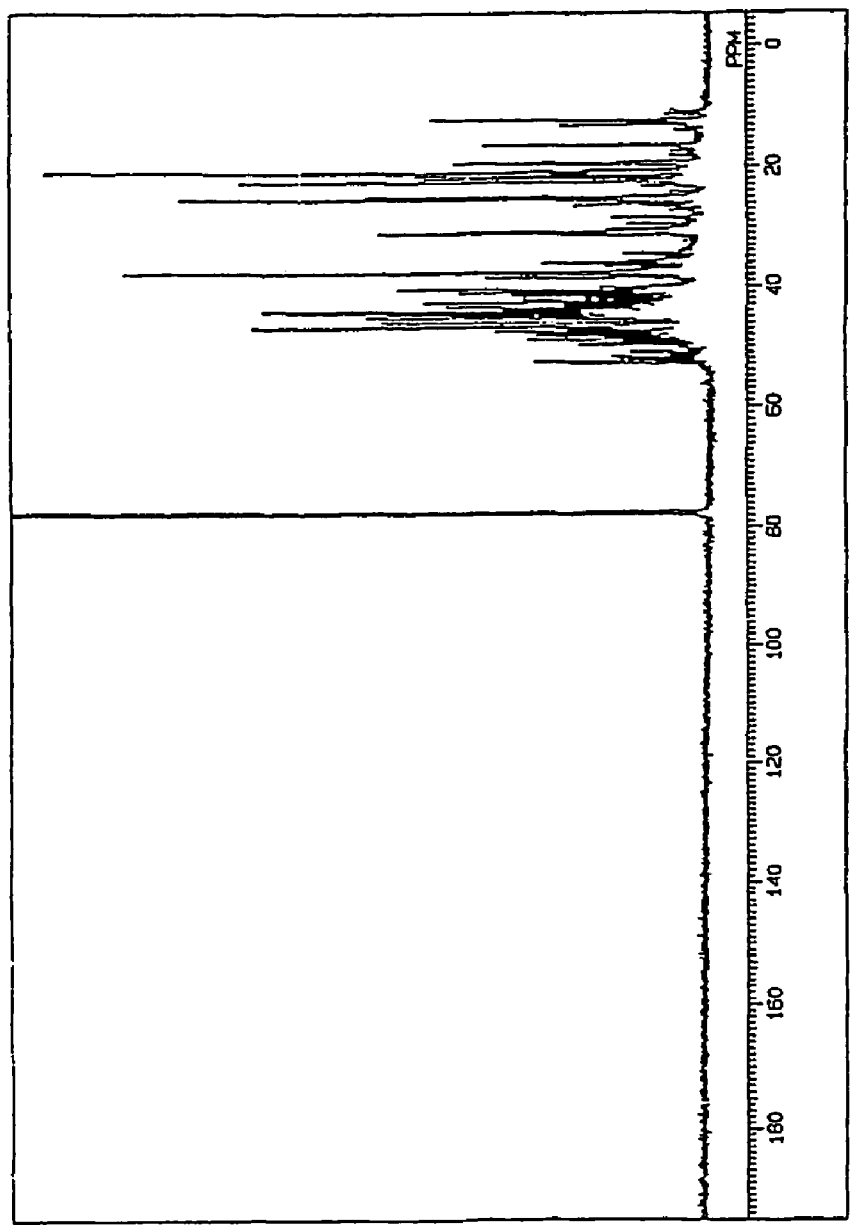
FIG. 4 shows a $^{13}$C-NMR spectrogram of a hydrogenation product of a trimer.

Into a 500 ml four-necked flask, 4.0 g of boron trifluoride diethyl etherate and 200 g of the olefin compound obtained above were placed. The resultant mixture was stirred by a mechanical stirrer at 20° C. for 6 hours, and the oligomerization was conducted. The obtained reaction mixture was washed with a dilute aqueous solution of sodium hydroxide and a saturated aqueous solution of sodium chloride. Into a 1 liter autoclave, 6 g of a nickel/diatomaceous earth catalyst for hydrogenation (manufactured by NIKKI CHEMICAL Co., Ltd.; N-113) was added, and the hydrogenation of the reaction mixture obtained above was conducted under a hydrogen pressure of 2.94 MPa·G at a temperature of 250° C. for a time of 5 hours. After the reaction was completed, the catalyst was removed by filtration. The filtrate was distilled under a reduced pressure, and 30 g of a hydrogenation product of the trimer was obtained as a fraction having a boiling point of 240 to 250° C./1.33 kPa. In accordance with the mass chromatography, the mass spectrography and the nuclear magnetic resonance spectrography, the hydrogenation product of the trimer was identified to be 3-methyl-2-[(3-methylbicyclo[2.2.1]-hept-2-yl)methyl]-2-[(2,3-dimethylbicyclo[2.2.1]hept-2-yl)methyl]bicyclo[2.2.1]heptane. The mass chromatogram of this compound is shown in FIG. 1, the mass spectrogram is shown in FIG. 2, the $^1$H-NMR spectrogram is shown in FIG. 3, and the $^{13}$C-NMR spectrogram is shown in FIG. 4. The properties are shown in Table 1.

COMPARATIVE EXAMPLE 1

The properties of a polybutene (manufactured by IDEMITSU PETROCHEMICAL Co., Ltd.; 100H) are shown in Table 1.

COMPARATIVE EXAMPLE 2

The properties of an ethylene-propylene oligomer (manufactured by MITSUI CHEMICALS Co., Ltd.; LUCANT HC600) are shown in Table 1.

COMPARATIVE EXAMPLE 3

The properties of a poly-α-olefin (manufactured by AMOCO Company; DURASYN 180) are shown in Table 1.

TABLE 1

|  | Example 1 | Comparative Example 1 | Comparative Example 2 | Comparative Example 3 |
|---|---|---|---|---|
| Kinematic viscosity (@ 40° C.) mm²/s | 11,000 | 6,800 | 9,850 | 1,250 |
| Kinematic viscosity (@ 100° C.) mm²/s | 51 | 210 | 600 | 100 |
| Viscosity index | −500 | 124 | 240 | 168 |
| Aniline point ° C. | 83 | 160 | 170 | 155 |

INDUSTRIAL APPLICABILITY

The bicyclo[2.2.1]heptane derivative of the present invention exhibits excellent compatibility with various organic compounds, has a small viscosity index and is used as the high viscosity hydrocarbon base material used for tackfiers for adhesives and process oils for rubber and resins.

The invention claimed is:

1. A composition comprising at least 81% of a bicyclo[2.2.1]heptane compound represented by the following general formula (1):

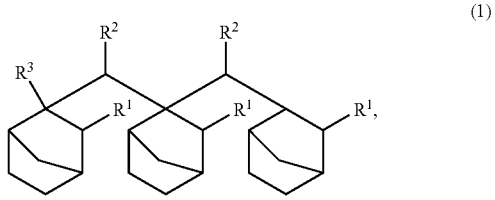

(1)

wherein $R^1$ and $R^2$ each represent hydrogen atom or methyl group, and $R^3$ represents methyl group or ethyl group.

2. The composition according to claim 1, which comprises a compound of formula (I) that is 3-methyl-2-[(3-methylbicyclo[2.2.1]hept-2-yl)methyl]-2-[(2,3-dimethylbicyclo[2.2.1]-hept-2-yl)methyl]bicyclo[2.2.1]heptane.

3. The composition according to claim 1, which comprises a compound of formula (I), which has a boiling point ranging from 240 to 250° C. at 1.33 kPa.

4. The composition of claim 1 which that comprises a compound of formula (I), wherein $R^1$ is hydrogen.

5. The composition of claim 1 that comprises a compound of formula (I), wherein $R^1$ is methyl.

6. The composition of claim 1 that comprises a compound of formula (I), wherein $R^2$ is hydrogen.

7. The composition of claim 1 that comprises a compound of formula (I), wherein $R^2$ is methyl.

8. The composition of claim 1 that comprises a compound of formula (I), wherein $R^3$ is methyl.

9. The composition of claim 1 that comprises a compound of formula (I), wherein $R^3$ is ethyl.

10. A tackifier composition comprising the composition of claim 1.

11. An adhesive composition comprising the composition of claim 1.

12. A process oil composition comprising the composition of claim 1.

13. A method for making a tackifier comprising incorporating the composition of claim 1 into a tackifier.

14. A method for making a process oil for rubber or resin comprising incorporating the composition of claim 1 into said process oil.

15. A process for preparing a composition containing at least 81% of a bicyclo[2.2.1]heptane compound which compound has a boiling point ranging from 240 to 250° C. at 1.33 kPa, comprising:
（a) preparing a trimer by trimerization of a material olefin selected from the group consisting of bicyclo[2.2.1]heptanes having a methyl group and a methylene group, bicyclo[2.2.1]heptanes having a methylene group, bicyclo[2.2.1]heptanes having an ethylidene group, bicyclo[2.2.1]hept-2-enes having methyl group, and bicyclo[2.2.1]hept-2-enes having an ethyl group;
(b) hydrogenating the trimer; and
(c) distilling the hydrogenation product of the trimer.

16. The process according to claim 15, wherein the material olefin is a dehydration product of 2-hydroxymethy-3-methylcyclo[2.2.1]heptane.

* * * * *